United States Patent
Luther et al.

[11] Patent Number: 6,045,734
[45] Date of Patent: Apr. 4, 2000

[54] PROCESS OF MAKING A CATHETER

[75] Inventors: Ronald B. Luther, Newport Beach; Richard A. Overton, Anaheim; Charles W. Dickerson, Tustin, all of Calif.; Lane Keith, Chattanooga; Ron Roth, Signal Mountain, both of Tenn.; Bruce Nichols, Chattanooga, Tenn.

[73] Assignee: Becton Dickinson and Company, Franklin Lakes, N.J.

[21] Appl. No.: 09/313,810

[22] Filed: May 18, 1999

Related U.S. Application Data

[63] Continuation of application No. 08/999,762, Nov. 11, 1997, abandoned, which is a continuation-in-part of application No. 08/449,540, May 24, 1995, abandoned.

[51] Int. Cl.[7] .......................... B29C 47/06; B32B 31/30
[52] U.S. Cl. ................ 264/103; 264/171.27; 264/173.11
[58] Field of Search .............................. 264/103, 171.27, 264/173.11

[56] References Cited

U.S. PATENT DOCUMENTS

| | | | |
|---|---|---|---|
| D. 272,651 | 2/1984 | Mahurker | D24/54 |
| 561,059 | 5/1896 | Mitchell et al. | |
| 3,225,762 | 12/1965 | Guttman | 128/214 |
| 3,352,306 | 11/1967 | Hirsch | 128/214.4 |
| 3,463,152 | 8/1969 | Sorenson | 128/214.4 |
| 3,630,195 | 12/1971 | Santomieri | 128/133 |
| 3,834,380 | 9/1974 | Boyd | 128/133 |
| 4,134,402 | 1/1979 | Mahurkar | 128/214 R |
| 4,194,504 | 3/1980 | Harms et al. | 128/214.4 |
| 4,249,541 | 2/1981 | Pratt | 128/753 |
| 4,327,722 | 5/1982 | Groshong et al. | 128/214.4 |
| 4,353,369 | 10/1982 | Muetterties | 128/214.4 |
| 4,392,856 | 7/1983 | Lichtenstein | 604/177 |
| 4,431,426 | 2/1984 | Groshong et al. | 604/280 |
| 4,434,810 | 3/1984 | Atkinson | 137/493 |
| 4,439,583 | 3/1984 | Gould et al. | 525/127 |
| 4,449,973 | 5/1984 | Luther | 604/161 |
| 4,525,157 | 6/1985 | Vaillancourt | 604/52 |
| 4,529,399 | 7/1985 | Groshong et al. | 604/53 |
| 4,549,879 | 10/1985 | Groshong et al. | 604/247 |
| 4,559,046 | 12/1985 | Groshong et al. | 604/282 |
| 4,568,329 | 2/1986 | Mahurkar | 604/43 |
| 4,583,968 | 4/1986 | Mahurkar | 604/43 |
| 4,588,398 | 5/1986 | Daugherty et al. | 604/265 |
| 4,623,327 | 11/1986 | Mahurkar | 604/4 |
| 4,627,841 | 12/1986 | Dorr | 604/158 |
| 4,668,225 | 5/1987 | Russo et al. | 604/270 |
| 4,671,795 | 6/1987 | Mulchin | 604/281 |
| 4,671,796 | 6/1987 | Groshong et al. | 604/247 |
| 4,690,675 | 9/1987 | Katz | 604/177 |
| 4,692,141 | 9/1987 | Mahurkar | 604/43 |
| 4,701,166 | 10/1987 | Groshong et al. | 604/247 |
| 4,728,322 | 3/1988 | Walker et al. | 604/165 |
| 4,753,640 | 6/1988 | Nichols et al. | 604/247 |
| 4,770,652 | 9/1988 | Mahurkar | 604/4 |
| 4,770,655 | 9/1988 | Haber et al. | 604/110 |
| 4,772,264 | 9/1988 | Cragg | 604/158 |
| 4,772,276 | 9/1988 | Wiita et al. | 604/283 |

(List continued on next page.)

FOREIGN PATENT DOCUMENTS

| | | |
|---|---|---|
| 247590 | 12/1987 | European Pat. Off. . |
| WO900734 | 9/1990 | WIPO . |
| WO9320881 | 10/1993 | WIPO . |

OTHER PUBLICATIONS

Landmark Venous Access Device, Menlo Care, Inc., 2 pages (no date) (copy previously sent).

*Primary Examiner*—Leo B. Tentoni
*Attorney, Agent, or Firm*—Stetina Brunda Garred & Brucker

[57] ABSTRACT

A catheter for intravascular use including an inner sleeve defining a hollow lumen and a middle sleeve which is disposed on the inner sleeve and includes a braided metal wire layer. Disposed on the middle sleeve is an outer sleeve which is preferably fabricated from a polyurethane material. The catheter has an outer diameter of 0.010 to 0.035 inches and a wall thickness which does not exceed 0.0035 inches.

12 Claims, 1 Drawing Sheet

U.S. PATENT DOCUMENTS

| Patent # | Date | Inventor | Class |
|---|---|---|---|
| 4,773,901 | 9/1988 | Norton | 604/265 |
| 4,798,597 | 1/1989 | Vaillancourt | 604/270 |
| 4,808,155 | 2/1989 | Mahurkar | 604/43 |
| 4,828,549 | 5/1989 | Kvalo | 604/164 |
| 4,842,582 | 6/1989 | Mahurkar | 604/43 |
| 4,846,799 | 7/1989 | Tanaka et al. | 604/158 |
| 4,846,812 | 7/1989 | Walker et al. | 604/264 |
| 4,863,432 | 9/1989 | Kvalo | 604/177 |
| 4,887,998 | 12/1989 | Martin et al. | 604/110 |
| 4,895,561 | 1/1990 | Mahurkar | 604/43 |
| 4,895,564 | 1/1990 | Farrell | 604/164 |
| 4,898,591 | 2/1990 | Jang et al. | 604/282 |
| 4,911,691 | 3/1990 | Aniuk et al. | 604/164 |
| 4,917,671 | 4/1990 | Chang | 604/168 |
| 4,927,415 | 5/1990 | Brodsky | 604/164 |
| 4,944,728 | 7/1990 | Carrell et al. | 604/164 |
| 4,950,252 | 8/1990 | Luther et al. | 604/198 |
| 4,955,863 | 9/1990 | Walker et al. | 604/165 |
| 4,973,319 | 11/1990 | Melsky | 604/247 |
| 4,976,704 | 12/1990 | McLees | 604/265 |
| 4,986,814 | 1/1991 | Burney et al. | 604/164 |
| 4,994,046 | 2/1991 | Wesson et al. | 604/198 |
| 4,995,863 | 2/1991 | Nichols et al. | 604/247 |
| 4,998,919 | 3/1991 | Schnepp-Pesch | 604/164 |
| 5,002,533 | 3/1991 | Jullien | 604/110 |
| 5,026,353 | 6/1991 | Bartman | 604/192 |
| 5,030,210 | 7/1991 | Alchas | 604/247 |
| 5,037,402 | 8/1991 | Bartman | 604/198 |
| 5,112,312 | 5/1992 | Luther | 604/177 |
| 5,120,317 | 6/1992 | Luther | 604/158 |
| 5,135,502 | 8/1992 | Koenig, Jr. | 604/164 |
| 5,147,332 | 9/1992 | Moorehead | 604/247 |
| 5,160,325 | 11/1992 | Nichols | 604/247 |
| 5,178,158 | 1/1993 | deToledo | 128/772 |
| 5,197,951 | 3/1993 | Mahurkar | 604/93 |
| 5,205,829 | 4/1993 | Lituchy | 604/164 |
| 5,205,834 | 4/1993 | Moorehead | 604/247 |
| 5,221,255 | 6/1993 | Mahurkar et al. | 604/43 |
| 5,221,256 | 6/1993 | Mahurkar | 604/43 |
| 5,224,938 | 7/1993 | Fenton, Jr. | 604/247 |
| 5,261,885 | 11/1993 | Lui | 604/247 |
| 5,273,540 | 12/1993 | Luther et al. | 604/110 |
| 5,304,155 | 4/1994 | Lui | 604/247 |
| 5,312,356 | 5/1994 | Engelson et al. | 604/164 |
| 5,338,295 | 8/1994 | Cornelius et al. | 604/96 |
| 5,374,245 | 12/1994 | Mahurkar | 604/43 |
| 5,378,230 | 1/1995 | Mahurkar | 604/43 |
| 5,389,074 | 2/1995 | Parker et al. | 604/96 |
| 5,397,307 | 3/1995 | Goodin | 604/96 |
| 5,439,445 | 8/1995 | Kontos | 604/96 |
| 5,441,489 | 8/1995 | Utsumi et al. | 604/280 |
| 5,462,523 | 10/1995 | Samson et al. | 604/30 |
| 5,486,159 | 1/1996 | Mahurkar | 604/4 |
| 5,522,807 | 6/1996 | Luther | 604/264 |
| 5,531,715 | 7/1996 | Engelson et al. | 604/265 |
| 5,538,513 | 7/1996 | Okajima | 604/282 |
| 5,554,136 | 9/1996 | Luther | 604/264 |
| 5,554,139 | 9/1996 | Okajima | 604/282 |
| 5,556,414 | 9/1996 | Turi | 606/198 |
| 5,792,401 | 8/1998 | Burnham | 264/103 |

PROCESS OF MAKING A CATHETER

CROSS-REFERENCE TO RELATED APPLICATIONS

The present application is a continuation of U.S. patent application Ser. No. 08/999,762 entitled SMALL DIAMETER INTRAVASCULAR CATHETER, filed Nov. 11, 1997, now abandoned which was a continuation of U.S. patent application Ser. No. 08/449,540 entitled SMALL DIAMETER INTRAVASCULAR CATHETER, filed May 24, 1995, now abandoned.

FIELD OF THE INVENTION

The present invention relates generally to intravascular catheters, and more particularly to a small diameter catheter for use in relation to neonatal care.

BACKGROUND OF THE INVENTION

The insertion of catheters into blood vessels or other anatomical passageways to facilitate the injection or withdrawal of fluids, or to maintain the passageway in an unobstructed condition is well known in the prior art. In this respect, catheters are commonly used to deliver contrast media into blood vessels for diagnostic purposes (e.g., to introduce radiopaque liquid into a particular artery for allowing an X-ray image to be taken for accessing the condition of the artery). Catheters are also commonly utilized to infuse various drugs and medications into a blood vessel, and for facilitating the withdrawal of infected bodily fluids from a particular site via suctioning. In addition to the foregoing applications, those of ordinary skill in the art will recognize that catheters are also used in other infusion and drainage applications as well.

A major problem associated with the design of catheters is the conflicting design requirements which are often encountered. In this respect, once the catheter is inserted into a blood vessel, it must possess sufficient flexibility to enable it to be advanced along a curved, tortuous path, yet be rigid enough so as not to undergo any appreciable buckling or permanent deformation which results in "kinking". Because of their lack of structural rigidity, the introduction of prior art catheters into a blood vessel or other anatomical passageway is typically accomplished by the advancement thereof over a guidewire or stylet of greater rigidity. In this respect, upon the advancement of the distal end of the catheter to a desired location within a passageway, the guidewire or stylet is withdrawn, with the catheter being maintained in its operative position.

In the design of catheters for neonatal applications, it is desirable for the distal end or tip of the catheter to be fabricated from or covered with a material which is softer than the material used to fabricate the remainder of the catheter so as to minimize any trauma to the interior walls of the blood vessel or other anatomical passageway into which the catheter is inserted. To this end, various types of materials of differing hardness may be used in the manufacture of such catheters. It is also desirable for the catheter to be formed in a manner such that the outer diameter thereof is small enough to fit inside the lumen of a very small artery, vein or other anatomical passageway without requiring a large access or entry incision. The lumen of the catheter is preferably formed to have as large a diameter as possible so as to maximize the rate of fluid flow therethrough. However, the fluid flow rate through prior art small diameter catheters is typically so low that the infusion of liquids therethrough must be accomplished via an intravenous pump which is fluidly coupled to the proximal end of the catheter.

Though prior art small diameter catheters must typically be coupled to an intravenous pump to facilitate the flow of liquids therethrough at an acceptable flow rate, the walls of such catheters can often only withstand a fluid pressure of approximately 30 psi before bursting. As such, it is also desirable for small diameter neonatal catheters to possess sufficient strength to resist bursting at those pressures to which the catheter may be subjected by an intravenous pump. The strength of the catheter wall must also be sufficient so as not to shear or rupture during the insertion of the catheter into the blood vessel or other anatomical passageway. Further, it is desirable for the outer surface of the catheter to be formed to be as smooth and uniform as possible so as to facilitate the laminar flow of blood thereover, thus drastically reducing occurrences of medical complications such as blood clots.

As such, the design of catheters for medical applications pertaining to newborn infants, and particularly those infants born prematurely, poses particularly difficult design problems. As previously indicated, the catheters must be designed for insertion into extremely small diameter blood vessels, which are particularly delicate and vulnerable to injury. Those prior art catheters which are specifically constructed for insertion into very small diameter anatomical passageways as are needed for neonatal care applications generally fail to fulfill many of the previously discussed design requirements. Most often, the prior art small diameter catheters are extremely susceptible to shearing failure and/or provide inadequate flow capacity.

In view of the deficiencies associated with those prior art catheters of small diameter, there is a need for a catheter for use in neonatal care applications which is adapted to minimize the trauma associated with the introduction thereof into the body of an infant, while providing maximum effectiveness in relation to treatment and diagnosis. The catheter constructed in accordance with the present invention is provided with an extremely small outer diameter dimension, and a smooth outer surface such that the effects of the insertion thereof into the body of the infant are minimized. The catheter constructed in accordance with the present invention is also resistant to kinking, shearing, and bursting, all of which are occurrences which can seriously damage the anatomical passageway into which the catheter is inserted, or other internal organs. In addition to the foregoing, the catheter constructed in accordance with the present invention also facilitates high volume, high-pressure fluid flow therethrough, with minimal resistance from the inner wall of the catheter. The present catheter is also maneuverable, which enables the same to be precisely positioned within an anatomical passageway. The present catheter also satisfies radiopacity requirements, especially necessary in catheters greater than 3 inches in length. Moreover, the present catheter is relatively inexpensive to manufacture.

SUMMARY OF THE INVENTION

In accordance with the present invention, there is provided a small diameter catheter for intravascular use having proximal and distal ends, and a distal tip portion adjacent the distal end. The catheter comprises an inner sleeve which defines a hollow lumen and is preferably fabricated from polytetrafluoroethylene. In the preferred embodiment, the inner sleeve has a wall thickness of 0.0005 to 0.001 inches, with the lumen thereof having a diameter of 0.005 to 0.030 inches. Disposed on the inner sleeve is a middle sleeve which comprises braided metal wire. The metal wire has a rectangular cross-sectional configuration, with a preferred width of approximately 0.003 inches and a preferred thickness of approximately 0.0007 inches. The distance separating the adjacent, parallel segments of the braided metal wire is preferably from 0.003 to 0.015 inches, and is directly proportional to the structural rigidity of the middle sleeve. In this respect, a increase in the separation distance increases the flexibility of the middle sleeve, with an decrease in the separation distance decreasing the flexibility of the middle sleeve. Disposed on the middle sleeve of the catheter is an outer sleeve. The outer sleeve of the catheter is preferably fabricated from a polyurethane material having a wall thickness of 0.0005 to 0.002 inches. In the preferred embodiment, the outer sleeve is fabricated from a hydrophilic polyurethane material along the distal tip portion of the catheter, and a hydrophobic polyurethane material along the remainder of the catheter. The catheter of the present invention may further include a layer of hydrogel Material which is disposed on the outer sleeve.

In the catheter constructed in accordance with the present invention, the distal end may be closed by an end cap attached thereto, with the distal tip portion extending approximately 0.50 inches proximally from the distal end and including a plurality of apertures disposed therein. The apertures are preferably arranged in a spiral pattern about the distal tip portion, with the combined area of the apertures being approximately twice the cross-sectional area of the catheter lumen. The apertures are preferably formed by a laser cutting process, and are used to facilitate the outflow of fluid from within the lumen of the catheter. Alternatively, the distal end of the catheter may be open.

Further in accordance with the present invention, there is provided a method for forming a small diameter catheter which comprises the steps of applying a first layer of material to an elongate mandrel having a circular cross-sectional configuration and a diameter of 0.005 to 0.030 inches, and subsequently applying a second layer of material to the first layer. The preferred method further comprises the steps of applying a third layer of material to the second layer, and removing the catheter from the mandrel, with the formed catheter having a preferred outer diameter of 0.010 to 0.035 inches and a preferred wall thickness which does not exceed 0.0035 inches. The method further comprises the steps of attaching an end cap to the catheter, and forming one or more fluid outflow apertures in the catheter.

BRIEF DESCRIPTION OF THE DRAWINGS

These, as well as other features of the present invention, will become more apparent upon reference to the drawings wherein.

DETAILED DESCRIPTION OF THE PREFERRED EMBODIMENT

Figure 1:
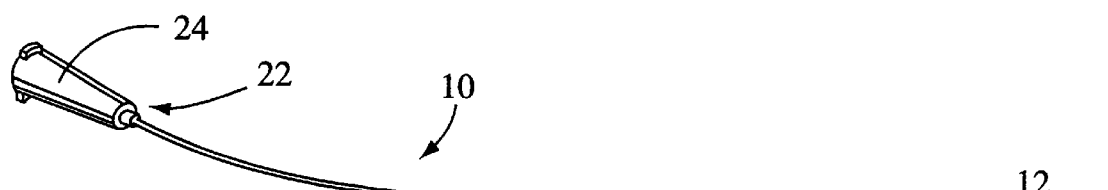
FIG. 1 is a perspective view of a small diameter catheter constructed in accordance with the present invention.

Referring now to the drawings wherein the showings are for purposes of illustrating a preferred embodiment of the present invention only, and not for purposes of limiting the same, FIG. 1 perspectively illustrates a small diameter catheter 10 constructed in accordance with the present invention. In FIG. 1, the catheter 10 is shown with a needle inserter 12 with which it is typically utilized. The inserter 12 comprises a pair of gripping wings 14 and a hollow, splitable needle 16 which extends axially from a cylindrical projection 18 formed on the gripping wings 14. The catheter 10 defines a distal end 20 which is extended into the inserter 12, and a proximal end 22 which is fluidly connected to a funnel 24.

To facilitate the introduction of the catheter 10 into a patient, the gripping wings 14 of the inserter 12 are grasped by the medical practitioner, with the needle 16 being inserted into a target blood vessel or other anatomical passageway. Subsequent to such insertion, the catheter 10 is advanced through the inserter 12 and needle 16 thereof into the blood vessel or other anatomical passageway, and manipulated until such time as the distal end 20 reaches a desired, operative position therewithin. After the distal end 20 of the catheter 10 has been properly positioned, the gripping wings 14 of the inserter 12 are again grasped to facilitate the withdrawal of the needle 16 from within the blood vessel or other anatomical passageway. Importantly, the catheter 10 remains in its operative position, with the inserter 12 (including the needle 16) being advanced longitudinally along the catheter 10 toward the proximal end 22 thereof.

Once the inserter 12 has been retracted a sufficient distance along the length of the catheter 10, the gripping wings 14 are separated from each other and pulled in opposite directions, thus "splitting" the needle 16 and facilitating the complete removal of the inserter 12 from the catheter 10. Though not shown, the needle 16 is scored in a manner which allows the same to be split by the pulling of the gripping wings 14. A more detailed discussion regarding the basic structure of the inserter 12 is found in Applicant's U.S. Pat. No. 4,449,973 issued May 22, 1984 and entitled "SMALL GAUGE, PRE-SPLIT CANNULA AND PROCESS FOR MANUFACTURE". Subsequent to the removal of the inserter 12 from the catheter 10, medications or other fluids are filled into the funnel 24 and transported to a desired internal site via the catheter 10. Radiographic contrast media is generally not among the fluid delivered through the catheter 10, as the wire braid 32 provides sufficient radiopacity. Once the distal end 20 of the catheter 10 has reached its operative position, merely raising the funnel 24 to a level above that of the distal end 20 is often sufficient to facilitate the necessary rate of fluid flow through the catheter 10. However, if desired, the rate of fluid flow may be increased through the utilization of a pump operatively coupled to the funnel 24. Additionally, the catheter 10 may be coated with a hydrogel prior to being inserted into the patient for purposes of enabling the same to slide more easily through the blood vessel or other anatomical passageway.

Figure 2:
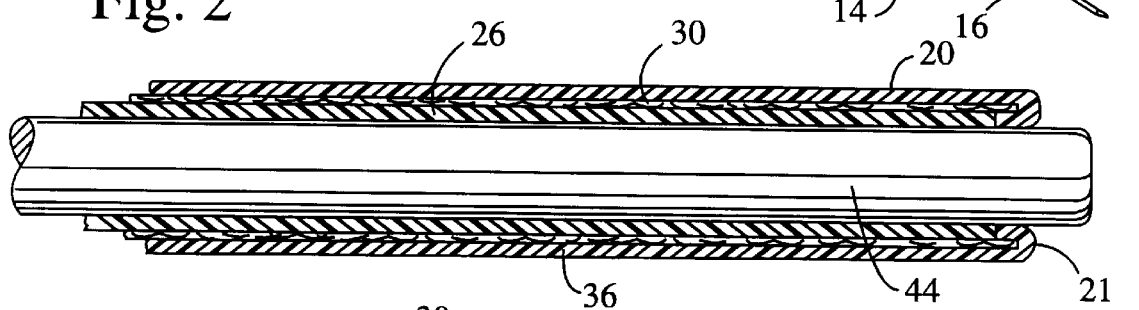
FIG. 2 is a partial cross-sectional view of the catheter during the fabrication thereof upon a mandrel.
Figure 3:
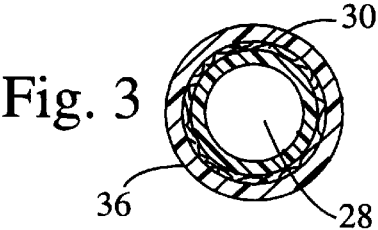
FIG. 3 is a cross-sectional view of the catheter shown in FIG. 1.

Referring now to FIGS. 2 and 3, the catheter 10 constructed in accordance with the present invention comprises an inner sleeve 26 which defines a hollow lumen 28 extending longitudinally therethrough. In the preferred embodiment, the inner sleeve has a wall thickness of 0.0005 to 0.001 inches, with the lumen 28 of the inner sleeve 26 having a diameter of 0.005 to 0.030 inches. The inner sleeve 26 is preferably fabricated from polytetrafluoroethylene (PTFE) which is commercially available as Teflon®, although alternative materials possessing similar properties may also be utilized. Importantly, the fabrication of the inner sleeve 26 from Teflon® subjects the fluid flowing through the lumen 28 to minimal resistive frictional forces.

Figure 4:
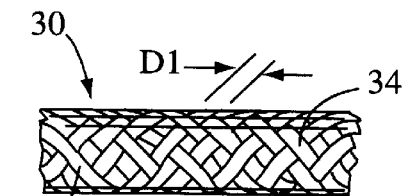
FIG. 4 is a partial side elevational view of the middle sleeve of the catheter which comprises a tightly woven braided metal wire layer.
Figure 6:
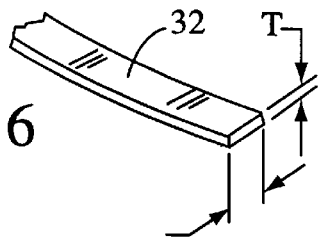
FIG. 6 is a partial perspective view of the wire used to fabricate the middle sleeve shown in FIGS. 4 and 5.
Figure 5:
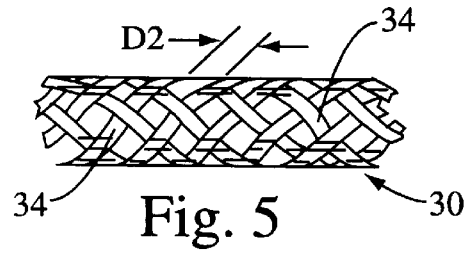
FIG. 5 is a partial side elevational view of the middle sleeve of the catheter which comprises a loosely woven braided metal wire layer.

Referring now to FIGS. 2–6, the catheter 10 further comprises a middle sleeve 30 which is disposed on the inner sleeve 26 and preferably comprises a layer of braided metal wire 32. As best seen in FIG. 6, the wire 32 preferably has a rectangular cross-sectional configuration, with a width W of approximately 0.003 inches and a thickness T of approximately 0.0007 inches. However, it will be recognized that the wire 32 may have alternative configurations and dimensions. As best seen in FIGS. 2 and 5, the wire 32 is interwoven to facilitate the formation of the middle sleeve 30. Importantly, the density of the wire weave (i.e., the number of wire segments 34 per inch) of the middle sleeve 30 may be varied according to the desired degree of flexibility thereof. In this respect, the flexibility of the middle sleeve 30 is proportional to the distance separating the center lines of adjacent, parallel pairs of the wire segments 34 thereof. As the distance separating the parallel pairs of wire segments 34 increases, the flexibility of the middle sleeve 30 increases with a decrease in the separation distance facilitating a decreased in the flexibility of the middle sleeve 30.

As shown in FIG. 4, the wire 32 is tightly woven to form the middle sleeve 30, with the distance D1 separating the adjacent, parallel wire segments 34 thereof being approximately 0.003 inches. As shown in FIG. 5, the wire 32 is loosely woven to form the middle sleeve 30, with the distance D2 separating the adjacent, parallel wire segments 34 thereof being approximately 0.015 inches. For the reasons previously discussed, the middle sleeve 30 shown in FIG. 4 is less flexible than that shown in FIG. 5 due to the wire 32 used to form the same being more tightly woven. If it is desired to provide the catheter 10 with decreased stiffness, (i.e., greater flexibility) the middle sleeve 30 may be fabricated in a manner shown in FIG. 5, As indicated above, less flexibility greater stiffness is imparted to the catheter 10 by fabricating the middle sleeve 30 thereof in the manner shown in FIG. 4.

In addition to the inner and middle sleeves 26, 30, the catheter 10 further comprises an outer sleeve 36 which is disposed on the middle sleeve 30. The outer sleeve 36 has a preferred wall thickness of 0.0005 to 0.002 inches, and is preferably fabricated from a polyurethane material. Polyurethane is the preferred material for the outer sleeve 36 due to the bio-compatibility thereof. It will be recognized that materials having characteristics similar to polyurethane may also be utilized to fabricate the outer sleeve 36.

In the catheter 10, the outer diameter of the outer sleeve 36, and hence the outer diameter of the catheter 10 itself, is preferably from 0.010 to 0.035 inches. Additionally, the wall thickness of the catheter 10 (i.e., the distance between the outer surface of the outer sleeve 36 and inner surface of the inner sleeve 26 defining the lumen 28) preferably does not exceed 0.0035 inches. The catheter 10 is typically fabricated to have a length from 2 to 24 inches, though other lengths are contemplated herein.

Figure 8:
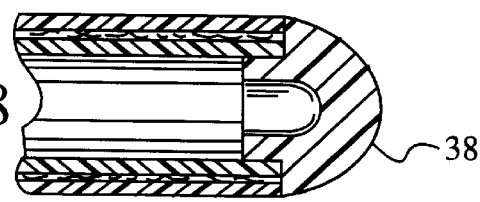
FIG. 8 is a cross-sectional view of the distal end of the catheter including the end cap.
Figure 7:
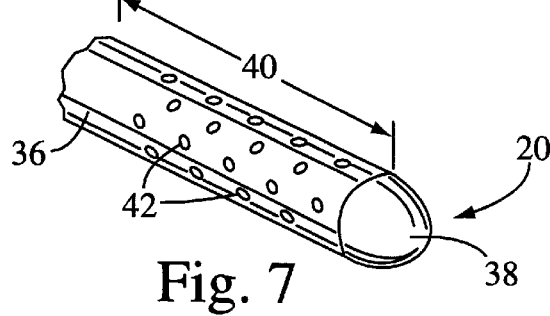
FIG. 7 is a partial perspective view of the distal tip portion of the catheter illustrating the fluid outflow apertures disposed in a spiral pattern therewithin.

Referring now to FIGS. 7 and 8, the distal end 20 of the catheter 10 is preferably closed, with such closure being facilitated by the attachment of an end cap 38 thereto. The end cap 38 is typically attached to the distal end 20 by a suitable adhesive. The catheter 10 defines a distal tip portion 40 which preferably extends approximately 0.25 inches proximally from the distal end 20 (i.e., the end cap 38). Disposed within the distal tip portion 40 are a plurality of fluid outflow apertures 42 which are preferably arranged in a spiral pattern thereabout. In the preferred embodiment, the apertures 42 are preferably formed via a laser or other precise drilling process, and each have a diameter of approximately 0.0005 to 0.005 inches. The number of apertures 42 included in the distal tip portion 40 is selected such that the combined area of the apertures 42 is approximately twice the cross-sectional area of the lumen 28. As will be recognized, these relative areas facilitate the outflow of fluid from the catheter 10 in an unobstructed manner. By incorporating the spirally arranged apertures 42 to facilitate the outflow of fluid from the lumen 28 rather than merely having the distal end 20 of the catheter being open (i.e., eliminating the end cap 38), a more even delivery of fluid from the catheter 10 is facilitated. Alternatively, referring to the distal end 20 of catheter 10 as shown in FIG. 2, the distal end 20 may be open, and preferably having the outer sleeve 20 heat formed to curl back inside the lumen 28 to define a smooth tip 21.

Though not shown, it is contemplated that the portion of the middle sleeve 30 extending along the distal tip portion 40 may be formed from wire 32 which is wound more tightly than in the remainder of the middle sleeve 30, thus increasing the stiffness of the distal tip portion 40. As will be recognized, such increased stiffness would allow the catheter 10 to be more easily advanced through the curved, tortuous path of a blood vessel or other anatomical passageway without inadvertently kinking. Additionally, it is contemplated that the portion of the outer sleeve 36 extending along the distal tip portion 40 may be fabricated from a hydrophilic polyurethane material, with the remainder of the outer sleeve 36 being fabricated from a hydrophobic polyurethane material. The increased softness of the hydrophilic polyurethane material used for the distal tip portion 40 of the outer sleeve 36 which occurs when the same is wetted by a bodily fluid reduces the risks of inadvertent injury to the wall of the blood vessel or other anatomical passageway as the catheter 10 is being advanced therethrough.

Referring now to FIG. 2, further in accordance with the present invention there is provided a method for forming the small diameter catheter 10. The method comprises the step of applying a first layer of material to an elongate mandrel 44 which has a circular cross-sectional configuration and a preferred diameter of 0.005 to 0.030 inches. As previously indicated, the first layer of material preferably comprises a layer of polytetrafluoroethylene which is applied to the mandrel 44 at a uniform thickness of 0.0005 to 0.001 inches. As will be recognized, the first layer of material cures to form the inner sleeve 26 of the catheter 10.

Subsequent to the application of the first layer of material to the mandrel 44, the metal wire 32 is machine wound about the first layer of material in a manner forming the braided middle sleeve 30. As previously discussed, the wire 32 may be loosely or tightly woven about the first layer of material depending on the desired flexibility of the catheter 10. In the preferred embodiment, the wire 32 is not wound about the first layer of material until the same has cured to form the inner sleeve 26.

Subsequent to the formation of the middle sleeve 30, a third layer of material is applied thereto. As also previously described, the third layer of material preferably comprises a layer of polyurethane material which is applied to the middle sleeve 30 at a uniform thickness of 0.0005 to 0.002 inches. As will be recognized, the third layer of material cures to form the outer sleeve 36 of the catheter 10. It will be recognized that the application of the third layer of material to the middle sleeve 30 may constitute a two-step process if the distal tip portion 40 thereof is formed from a hydrophilic polyurethane material with its remainder being formed from a hydrophobic polyurethane material.

After the third layer of material has cured to form the outer sleeve 36, the apertures 42 area then added to the distal tip portion 40 via the previously described laser drilling process. Thereafter, the catheter 10 is slidably removed from upon the mandrel 44, and the end cap 38 adhesively secured to the distal end 20 thereof. The catheter 10 formed from the aforementioned process has an outer diameter of 0.010 to 0.035 inches, and a wall thickness which does not exceed 0.0035 inches.

Advantageously, the catheter 10 constructed in accordance with the present invention, though being of extremely small diameter, has a high resistance to being inadvertently cut or sheared during insertion into a blood vessel or other anatomical passageway. In particular, the construction of the catheter 10 allows the same to withstand shear forces which are approximately ten times greater than those to which prior art plastic or silicone catheters of similar diameter can be subjected. In addition to being exceptionally strong, the catheter 10 possesses sufficient flexibility to enable the same to be selectively maneuvered through a curved, tortuous blood vessel or other anatomical passageway, yet possesses enough stiffness (due to the inclusion of the middle sleeve 30) so that a guidewire or stylet is usually not required to facilitate the advancement of the catheter 10 to a desired treatment site. Use of the polyurethane material for the outer sleeve 36 maximizes the bio-compatibility of the catheter 10, with the use of Teflon® for the inner sleeve 26 facilitating minimum resistive friction when fluid is channeled therethrough. In this respect, the catheter 10 of the present invention provides a gravity flow rate of approximately 18 cc per hour, and provides a flow rate of approximately 70 cc per hour when a pump providing approximately 6 psi pressure is operatively coupled to the funnel 24. Importantly, if the catheter 10 is operatively coupled to a pump, the construction thereof allows it to withstand fluid pressures of up to 200 psi without bursting.

Though usually not required, it will be recognized that the catheter 10 may be used in conjunction with a guidewire or stylet if desired. Due to it being radiopaque, the incorporation of the middle sleeve 30 comprising the braided metal wire layer into the catheter 10 also eliminates the need to include barium additives within the catheter 10 to show the position of the distal end 20 when the same is being advanced to a desired treatment site. Since the addition of barium to a catheter material reduces the strength thereof, the absence of barium in the catheter 10 further results in the strength thereof being increased over that associated with prior art catheters.

Additional modifications and improvements of the present may also be apparent to those skilled in the art. Thus, the particular combination of parts described and illustrated herein is intended to represent only one embodiment of the present invention, and is not intended to serve as limitations of alternative devices within the spirit and scope of the invention.

What is claimed is:

1. A method of forming a flexible catheter for intravascular use, comprising the steps of:

(a) forming an inner sleeve which defines a catheter lumen extending longitudinally therethrough;

(b) forming a single layer of interwoven material radially upon the inner sleeve; and (c) forming an outer sleeve on the single layer of interwoven material, thereby forming a catheter having an inner sleeve, an outer sleeve, and a single layer of interwoven material therebetween.

2. The method of claim 1 wherein step (a) comprises:

(1) applying a first layer of a curable material to a mandrel; and (2) allowing the material of said first layer to cure.

3. The method of claim 2 wherein comprises applying a layer of said first layer is polytetrafluoroethylene applied to a thickness of about 0.0005 to about 0.001 inch.

4. The method of claim 2 wherein the mandrel has a circular cross-sectional configuration and a diameter of about 0.005 to about 0.030 inch.

5. The method of claim 2 wherein step (b) comprises tightly weaving the single layer of interwoven material to decrease the flexibility of the catheter.

6. The method of claim 1 wherein step (b) comprises loosely weaving the single layer of interwoven material to increase the flexibility of the catheter.

7. The method of claim 1 wherein step (b) comprises applying metal wire to the inner sleeve.

8. The method of claim 7 wherein step (b) comprises applying metal wire having a width of approximately 0.003 inches and a thickness of approximately 0.0007 inches to the inner sleeve.

9. The method of claim 7 wherein step (b) comprises machine winding the metal wire about the inner sleeve.

10. The method of claim 1 wherein step (c) comprises:

(1) applying a second layer of material to the single layer of interwoven material; and (2) allowing the second layer to cure.

11. The method of claim 10 wherein said second later is polyurethane material applied at a thickness of about 0.0005 to about 0.002 inch.

12. The method of claim 1 further comprising the step of:

(d) forming a plurality of fluid outflow apertures in the catheter.

* * * * *